United States Patent [19]

Wilson

[11] Patent Number: 5,674,917
[45] Date of Patent: Oct. 7, 1997

[54] SUPERABSORBENT HYDROPHILIC ISOCYANATE-BASED FOAM AND PROCESS FOR PRODUCTION THEREOF

[75] Inventor: Robert N. Wilson, Hixson, Tenn.

[73] Assignee: Woodbridge Foam Corporation, Mississauga, Canada

[21] Appl. No.: 413,433

[22] Filed: Mar. 30, 1995

[51] Int. Cl.$^6$ ................... C08J 9/04; C08J 9/08; A61F 13/15; A61L 15/26

[52] U.S. Cl. .......................... 521/109.1; 521/52; 521/99; 521/125; 521/134; 521/137; 521/139; 521/155; 521/163; 521/170; 521/172; 521/174; 521/905; 604/358; 604/369; 604/372; 604/374; 604/376

[58] Field of Search .................. 521/52, 99, 109.1, 521/125, 134, 137, 139, 155, 163, 170, 172, 174, 905; 604/358, 369, 372, 374, 376

[56] References Cited

U.S. PATENT DOCUMENTS

| | | | |
|---|---|---|---|
| 3,171,820 | 3/1965 | Volz | 521/61 |
| 3,175,025 | 3/1965 | Geen et al. | 264/80 |
| 3,781,231 | 12/1973 | Janssen et al. | 521/137 |
| 3,793,241 | 2/1974 | Kyle et al. | 521/159 |
| 3,799,898 | 3/1974 | Lamplugh et al. | 521/52 |
| 3,900,030 | 8/1975 | Bashan | 128/285 |
| 4,062,817 | 12/1977 | Westerman | 525/330.2 |
| 4,066,583 | 1/1978 | Spaulding | 526/238.23 |
| 4,167,464 | 9/1979 | George | 204/159.23 |
| 4,190,562 | 2/1980 | Westerman | 526/238.23 |
| 4,259,452 | 3/1981 | Yukuta et al. | 521/914 |
| 4,394,930 | 7/1983 | Korpman | 220/444 |
| 4,466,993 | 8/1984 | Hou et al. | 427/44 |
| 4,486,489 | 12/1984 | George | 428/220 |
| 4,725,629 | 2/1988 | Garvey et al. | 521/137 |
| 4,731,391 | 3/1988 | Garvey | 521/137 |
| 4,977,892 | 12/1990 | Ewall | 128/156 |
| 4,985,467 | 1/1991 | Kelly et al. | 521/109.1 |
| 5,328,935 | 7/1994 | Van Phan et al. | 521/150 |
| 5,336,695 | 8/1994 | Nass et al. | 521/137 |
| 5,338,766 | 8/1994 | Phan et al. | 521/149 |

FOREIGN PATENT DOCUMENTS

| | | |
|---|---|---|
| 1207486 | 7/1986 | Canada. |
| 1250190 | 2/1989 | Canada. |
| 0288865 | 11/1991 | European Pat. Off.. |
| 4233289 | 4/1994 | Germany. |
| 4308347 | 9/1994 | Germany. |
| 57-92032 | 6/1982 | Japan. |
| 1317930 | 5/1973 | United Kingdom. |
| 1354576 | 5/1974 | United Kingdom. |

OTHER PUBLICATIONS

"Urethane Chemicals Preliminary Data Sheet", Olin Urethane Chemical, date unknown.

"Scott Acquell Foam", Foam Division, Scott Paper Co., date unknown.

*Primary Examiner*—Rabon Sergent
*Attorney, Agent, or Firm*—Fitzpatrick, Cella, Harper & Scinto

[57] ABSTRACT

A foamed isocyanate-based polymer having a cellular structure and containing a superabsorbent material, the polymer being capable of: (i) absorbing at least about 20 times its weight of an aqueous fluid maintained at a temperature of from about 20° to about 25° C., and (ii) retaining at least about 20 times its weight of absorbed aqueous fluid which is bound to the superabsorbent material. A process for producing a foamed isocyanate-based polymer comprising the steps of: providing a substantially uniform mixture comprising an isocyanate, an active hydrogen-containing compound and a superabsorbent material, the superabsorbent material being capable of absorbing at least about 20 times its weight of an aqueous fluid maintained at a temperature in the range of from about 20° to about 25° C.; adding to the substantially uniform mixture an aqueous blowing agent and a catalyst to form a reaction mixture; and expanding the reaction mixture to produce the foamed isocyanate-based polymer; wherein the active hydrogen-containing compound comprises from about 10% to 100% by weight of a hydrophillic active hydrogen-containing compound and from 0 to about 90% by weight a non-hydrophillic active hydrogen-containing compound. The foamed isocyanate-based polymer is ideally suitable for use in an absorption layer in a personal hygiene device.

69 Claims, No Drawings

SUPERABSORBENT HYDROPHILIC ISOCYANATE-BASED FOAM AND PROCESS FOR PRODUCTION THEREOF

BACKGROUND OF THE INVENTION

1. Field of the Invention

The present invention relates to a foamed polymer and to a process for production thereof. More particularly, the present invention relates to a foamed isocyanate-based (e.g. polyurethane, polyurea, polyisocyanurate, etc.) polymer and a process for production thereof.

2. Description of the Prior Art

Isocyanate-based polymers are known in the art. Generally, those of skill in the art understand isocyanate-based polymers to be polyurethanes, polyureas, polyisocyanurates and mixtures thereof.

It is also known in the art to produce foamed isocyanate-based polymers. Indeed, one of the advantages of isocyanate-based polymers compared to other polymer systems is that the chemistry can be used to achieve desired product properties in situ.

One of the conventional ways to produce a polyurethane foam is known as the "one-shot" technique. In this technique, the isocyanate, a suitable polyol, a catalyst, water (which acts as a primary blowing agent and can optionally be supplemented with one or more secondary organic blowing agents) and other additives are mixed together at once using, for example, a mechanical or impingement mixer. Generally, if one were to produce a polyurea, the polyol would be replaced with a suitable polyamine. A polyisocyanurate may result from cyclotrimerization of the isocyanate component. Urethane-modified polyureas or polyisocyanurates are known in the art. In either scenario, the reactants would be intimately mixed very quickly using a suitable mixer.

Another technique for producing foamed isocyanate-based polymers is known as the "prepolymer" technique. In this technique, a prepolymer of polyol and isocyanate (in the case of a polyurethane) are reacted in an inert atmosphere to form a liquid polymer terminated with isocyanate groups. To produce the foamed polymer, the prepolymer is thoroughly mixed with a polyol (in the case of producing a polyurethane) or a polyamine (in the case of producing a polyurea) in the presence of a catalyst or a cross-linker.

As is known by those of skill in the art, many conventional isocyanate-based foams are non-hydrophilic (i.e. relatively hydrophobic). Such foams generally have an aversion to aqueous fluids. Practically, this results in such foams being unable to absorb or pick up significant quantities of aqueous fluids (e.g. the foams will float on water) other than by mechanical entrainment. Accordingly, such foams are virtually never used in an application in which significant fluid absorption is a desired feature.

Heretofore, the prior art has endeavoured to produce hydrophilic isocyanate-based foams (i.e. foams which are able to absorb or pick up significant quantities of aqueous fluids) using two general approaches.

The first approach has been to confer hydrophilicity to an otherwise hydrophobic foam by the use of specific active hydrogen-containing compound (e.g. polyol in the case of polyurethane) and/or another additive to the reaction system. For example, it is known that use of a polyol commercially available from Olin Corporation under the tradename POLY-G-X-609® in an otherwise conventional formulation will result in production of a hydrophilic polyurethane foam. See also, for other examples of this approach, U.S. Pat. Nos. 3,781,231 (Janssen et al.) and 3,799,898 (Lamplugh et al.), and British patent 1,354,576 (Fritz Nauer & Co.), the contents of each of which are hereby ..incorporated by reference. The resultant foam is hydrophilic in the sense that it will absorb or pick up an aqueous fluid (e.g. when the foam is immersed in a body of water is will be at least partially or totally submerged). However, the resultant foam is incapable of retaining substantial quantities of any absorbed or picked up aqueous fluid (e.g. in the previous example, when the at least partially or totally submerged foam is removed from the body of water, the absorbed water will immediately begin to drain from the foam matrix). The result of this is that, previously known hydrophilic foams produced according to the first approach are unsuitable for use in applications where aqueous fluid absorption and retention are required (e.g. disposable diapers, disposable training pants, sanitary napkins, incontinence devices and other personal hygiene products, general purpose sponges, surgical sponges, absorbant devices for agricultural/horticultural applications, pest control, chemical spill blockage and the like).

The second approach has been to combine a non-hydrophilic (i.e. relatively hydrophobic) isocyanate-based foam with a superabsorbent material. Generally, a material is considered superabsorbent if it will absorb a multiple of its weight of a fluid. Thus, most known superabsorbent materials are capable of absorbing at least about ten times, preferably at least about twenty times, their in weight of an aqueous fluid. For examples of this approach, see U.S. Pat. Nos. 3,900,030, 4,394,930 (Korpman), 4,731,391 (Garvey) and 4,985,467 (Kelly et al.), and published Japanese patent applications 55/168,104 and 57/92,032, the contents of each of which are hereby incorporated by reference. A general disadvantage of this approach is that aqueous fluid absorption occurs initially via the surface of the foam, the superabsorbent material therein expands thereby retarding migration of the fluid to the interior of the foam with the result that the amount of aqueous fluid absorption or pick up is significantly limited. The principal reason for this phenomenon is that the foam matrix has a cellular structure which is one or both of closed (this inhibits fluid absorption) or open (this allows fluid absorption). As is known in the art, an open cellular structure is one wherein a cellular structure is maintained and is open by virtue of providing fissures or cracks in the windows between the cell struts. The fissures or cracks result in cells which are effectively interconnected as regards fluid absorption or pick up. Kelly et al. is noteworthy since it endeavours to overcome the general disadvantage of this approach discussed above. Specifically, the purported novelty in Kelly et al. is produce a cellular structure containing the superabsorbent material and subjecting it to a thermal reticulation process with the result that the windows between the struts of a conventional cellular structure (closed or open) are completely destroyed allowing for improved fluid access to the interior of foam. The disadvantage of Kelly et al. is that in return for an extra complicated and expense process step, the gain in fluid absorption or pick up is modest, at best, and only at certain loadings of superabsorbent material. A further disadvantage of Kelly et al. is that production of a foam having reproducible and consistent physical properties is difficult.

In light of these difficulties in the prior art, it would be advantageous to have a foamed isocyanate-based polymer which is both hydrophilic and capable of retaining a substantial quantity of aqueous fluid which absorbed or picked up. It would be further advantageous if such a foam could be produced in a relatively uncomplicated way and possessed generally reproducible physical properties.

SUMMARY OF THE INVENTION

It is an object of the present invention to provide a novel foamed isocyanate-based polymer which obviates or mitigates one or more of the above-identified deficiencies of the prior art.

It is an object of the present invention to provide a novel process for producing such a foamed isocyanate-based polymer.

It is another object of the present invention to provide a novel personal hygiene device incorporating such a foamed isocyanate-based polymer.

Accordingly, in one of its aspects, the present invention provides a foamed isocyanate-based polymer having a cellular structure and containing a superabsorbent material, the polymer being capable of: (i) absorbing at least about 20 times its weight of an aqueous fluid maintained at a temperature of from about 20° to about 25° C., and (ii) retaining at least about 20 times its weight of absorbed aqueous fluid which is bound to the superabsorbent material.

In another of its aspects, the present invention provides a foamed polyurethane polymer comprising poly(acrylic acid alkali metal salt) in an amount in the range of from about 55 to about 65 parts by weight of polyol used to produce the foamed polyurethane polymer, the polymer being capable of: (i) absorbing from about 35 to about 65 times its weight of an aqueous fluid maintained at a temperature of from about 20° to about 25° C., and (ii) retaining from about 30 to about 55 times its weight of absorbed aqueous fluid which is bound to the poly(acrylic acid alkali metal salt).

In yet another of its aspects, the present invention provides a process for producing a foamed isocyanate-based polymer comprising the steps of:

providing a substantially uniform mixture comprising an isocyanate, an active hydrogen-containing compound and a superabsorbent material, the superabsorbent material being capable of absorbing at least about 20 times its weight of an aqueous fluid maintained at a temperature in the range of from about 20° to about 25° C.;

adding to the substantially uniform mixture an aqueous blowing agent and a catalyst to form a reaction mixture; and expanding the reaction mixture to produce the foamed isocyanate-based polymer;

wherein the active hydrogen-containing compound comprises from about 10% to 100% by weight of a hydrophilic active hydrogen-containing compound and from 0 to about 90% by weight a non-hydrophilic active hydrogen-containing compound.

In yet another of its aspects, the present invention provides a personal hygiene device having a bodily fluid absorbent layer consisting essentially of a foamed isocyanate-based polymer having a cellular structure and containing a superabsorbent material, the polymer being capable of: (i) absorbing at least about 20 times its weight of an aqueous fluid maintained at a temperature of from about 20° to about 25° C., and (ii) retaining at least about 20 times its weight of absorbed aqueous fluid which is bound to the superabsorbent material.

In yet another of its aspects, the present invention provides a personal hygiene device having a bodily fluid absorbent layer consisting essentially of a foamed polyurethane polymer comprising poly(acrylic acid alkali metal salt) in an amount in the range of from about 55 to about 65 parts by weight of polyol used to produce the foamed polyurethane polymer, the polymer being capable of: (i) absorbing from about 35 to about 65 times its weight of an aqueous fluid maintained at a temperature of from about 20° to about 25° C., and (ii) retaining from about 30 to about 55 times its weight of absorbed aqueous fluid which is bound to the poly(acrylic acid alkali metal salt).

As used throughout this specification, the term "isocyanate-based polymer" is intended to mean, inter alia, polyurethane, polyurea and polyisocyanurate.

It has been discovered that, by combining reactants necessary to produce a hydrophilic isocyanate-based foam with a superabsorbent material, a superabsorbent foam having surprising, unexpected and significantly enhanced aqueous fluid absorption/pick up (the terms absorption and pick up are used interchangeably throughout the present specification) and retention properties can be made. More specifically, many of the present foamed isocyanate-based polymers exhibit synergistic improvements in fluid absorption and retention properties compared to prior art hydrophilic foams which contain no superabsorbent material (i.e. the first approach of the prior art discussed above) and hydrophobic foams which contain superabsorbent materials (i.e. the second approach of the prior art discussed above). To the knowledge of the Applicant, prior to the present invention, foamed isocyanate-based polymers having such enhanced aqueous fluid absorption and retention properties were unknown.

While applications for such a foamed isocyanate-based polymer will be immediately apparent to those of skill in the art, it is believed that the present foamed isocyanate-based polymer is particularly useful in personal hygiene devices such as disposable diapers, disposable training pants, sanitary napkins, incontinence pads, bandage gauze and the like. More particularly, it is contemplated that the present foamed isocyanate-based polymer presents a significantly more cost effective alternative to the conventional superabsorbent material/pulp mixtures used in current disposable diapers. The significant costs savings is realized in both reduced components costs and equipment costs.

DETAILED DESCRIPTION OF THE PREFERRED EMBODIMENTS

The present invention is related to, inter alia, a foamed isocyanate-based polymer and to a process for production thereof. Generally, the isocyanate-based polymer is selected from the group comprising polyurethane, polyurea, polyisocyanurate, urea-modified polyurethane, urethane-modified polyurea, urethane-modified polyisocyanurate and urea-modified polyisocyanurate. The preferred foamed isocyanate-based polymer is selected from the group consisting of polyurethane and urea-modified polyurethane. The most preferred isocyanate-based polymer is polyurethane. As is known in the art, the term "modified", when used in conjunction with a polyurethane, polyurea or polyisocyanurate means that up to 50% of the polymer backbone forming linkages have been substituted.

The first step in the present process comprises providing a substantially uniform mixture comprising an isocyanate, an active hydrogen-containing compound and a superabsorbent material, the superabsorbent material being capable of absorbing at least about 20 times its weight of an aqueous fluid maintained at a temperature in the range of from about 20° to about 25° C.

The isocyanate suitable for use in the substantially uniform mixture is not particularly restricted and the choice thereof is within the purview of a person skilled in the art. Generally, the isocyanate compound suitable for use may be represented by the general formula:

$$Q(NCO)_i$$

wherein i is an integer of two or more and Q is an organic radical having the valence of i. Q may be a substituted or unsubstituted hydrocarbon group (e.g. an alkylene or arylene group). Moreover, Q may be represented by the general formula:

$$Q^1-Z-Q^1$$

wherein $Q^1$ is an alkylene or arylene group and Z is chosen from the group comprising —O—, —O—$Q^1$—, —CO—, —S—, —S—$Q^1$—S— and —SO$_2$—. Examples of isocyanate compounds which fall within the scope of this definition include hexamethylene diisocyanate, 1,8-diisocyanato-p-methane, xylyl diisocyanate, (OCNCH$_2$CH$_2$CH$_2$OCH$_2$O)$_2$, 1-methyl-2,4-diisocyanatocyclohexane, phenylene diisocyanates, toluene diisocyanates, chlorophenylene diisocyanates, diphenylmethane-4,4'-diisocyanate, naphthalene-1,5-diisocyanate, triphenylmethane-4,4',4''-triisocyanate and isopropylbenzene-alpha-4-diisocyanate.

In another embodiment, Q may also represent a polyurethane radical having a valence of i. In this case Q(NCO)$_i$ is a compound which is commonly referred to in the art as a prepolymer. Generally, a prepolymer may be prepared by reacting a stoichiometric excess of an isocyanate compound (as defined hereinabove) with an active hydrogen-containing compound (as defined hereinafter), preferably the polyhydroxyl-containing materials or polyols described below. In this embodiment, the polyisocyanate may be, for example, used in proportions of from about 30 percent to about 200 percent stoichiometric excess with respect to the proportion of hydroxyl in the polyol. The prepolymer may then be reacted with a polyol to produce a polyurethane foam or an amine to produce a polyurea-modified polyurethane.

In another embodiment, the isocyanate compound suitable for use in the process of the present invention may be selected from dimers and trimers of isocyanates and diisocyanates, and from polymeric diisocyanates having the general formula:

$$[Q'' (NCO)_i]_j$$

wherein both i and j are integers having a value of 2 or more, and Q'' is a polyfunctional organic radical, and/or, as additional components in the reaction mixture, compounds having the general formula:

$$L(NCO)_i$$

wherein i is an integer having a value of 1 or more and L is a monofunctional or polyfunctional atom or radical. Examples of isocyanate compounds which fall with the scope of this definition include ethylphosphonic diisocyanate, phenylphosphonic diisocyanate, compounds which contain a =Si—NCO group, isocyanate compounds derived from sulphonamides (QSO$_2$NCO), cyanic acid and thiocyanic acid.

See also for example, British patent No. 1,453,258, the contents of which are incorporated herein by reference.

Non-limiting examples of suitable isocyanates include: 1,6-hexamethylene diisocyanate, 1,4-butylene diisocyanate, furfurylidene diisocyanate, 2,4-toluene diisocyanate, 2,6-toluene diisocyanate, 2,4'-diphenylmethane diisocyanate, 4,4'-diphenylmethane diisocyanate, 4,4'-diphenylpropane diisocyanate, 4,4'-diphenyl-3,3'-dimethyl methane diisocyanate, 1,5-naphthalene diisocyanate, 1-methyl-2,4-diisocyanate-5-chlorobenzene, 2,4-diisocyanato-s-triazine, 1-methyl-2,4-diisocyanato cyclohexane, p-phenylene diisocyanate, m-phenylene diisocyanate, 1,4-naphthalene diisocyanate, dianisidine diisocyanate, bitoluene diisocyanate, 1,4-xylylene diisocyanate, 1,3-xylylene diisocyanate, bis-(4-isocyanatophenyl)methane, bis-(3-methyl-4-isocyanatophenyl)methane, polymethylene polyphenyl polyisocyanates and mixtures thereof. A more preferred isocyanate is selected from the group comprising 2,4-toluene diisocyanate, 2,6-toluene diisocyanate and mixtures thereof, for example, a mixture comprising from about 75 to about 85 percent by weight 2,4-toluene diisocyanate and from about 15 to about 25 percent by weight 2,6-toluene diisocyanate. Another more preferred isocyanate is selected from the group comprising 2,4'-diphenylmethane diisocyanate, 4,4'-diphenylmethane diisocyanate and mixtures thereof. The most preferred isocyanate is a mixture comprising from about 15 to about 25 percent by weight 2,4'-diphenylmethane diisocyanate and from about 75 to about 85 percent by weight 4,4'-diphenylmethane diisocyanate. An example of such an isocyanate is commercially available from Imperial Chemical Industries under the tradename Rubinate M and from The Dow Chemical Company under the tradename PAPI 4027.

The active hydrogen-containing compound used in the uniform mixture comprises from about 10% to 100% by weight of a hydrophilic active hydrogen-containing compound and from 0 to about 90% by weight a non-hydrophilic active hydrogen-containing compound. Preferably, the active hydrogen-containing compound comprises from about 20% to about 90%, more preferably from about 40% to about 90%, most preferably from about 70% to about 80%, by weight of a hydrophilic active hydrogen-containing compound and from about 10% to about 80%, more preferably from about 10% to about 60%, most preferably from about 20% to about 30%, by weight a non-hydrophilic active hydrogen-containing compound.

Preferably, the hydrophilic active hydrogen-containing compound is a hydrophilic polyol. Ideally the hydrophilic-polyol has a molecular weight in the range of from about 1500 to about 6000. Preferably, the hydrophilic polyol is selected from the group consisting of diols, triols, tetrols and mixtures thereof, each of which contain polyoxyalkylene groups, the polyoxyalkylene groups comprising at least about 25, more preferably from about 40 to about 85, most preferably from about 55 to about 85, percent by weight of ethylene oxide. As is known in the art, the balance of the polyoxyalkylene groups is conventionally made up of one or both of propylene oxide and butylene oxide, preferably solely propylene oxide. A particularly preferred hydrophilic polyol is commercially available from The Dow Chemical Company under the tradename CP1421.

The non-hydrophilic active hydrogen-containing compound, if present, is selected from the group consisting of non-hydrophilic polyols, polyamines, polyamides, polyimines, polyolamines and mixtures thereof.

If the process is utilized to produce a polyurethane foam, the non-hydrophilic active hydrogen-containing compound is typically a non-hydrophilic polyol. Generally, if such non-hydrophilic polyols contain or are based on ethylene oxide, the ethylene oxide will be present in amounts of less than about 20% by weight. The choice of such a polyol is not particularly restricted and is within the purview of a person skilled in the art. For example, the polyol may be a hydroxyl-terminated backbone of a member selected from the group comprising polyether, polyester, polycarbonate, polydiene and polycaprolactone. The polyol may be selected from the group comprising hydroxyl-terminated polyhydrocarbons, hydroxyl-terminated polyformals, fatty acid triglycerides, hydroxyl-terminated polyesters, hydroxymethyl-terminated polyesters, hydroxymethyl-terminated perfluoromethylenes, polyalkyleneether glycols, polyalkylenearyleneether glycols and polyalkyleneether triols. The polyol may also be selected from the group comprising adipic acid-ethylene glycol polyester, poly(butylene glycol), poly(propylene glycol) and hydroxyl-terminated polybutadiene—see, for example, British patent No. 1,482,213, the contents of which are incorporated herein by reference. Preferably, such a polyol has a molecular weight in the range of from about 200 to about 10,000, more preferably from about 1,500 to about 4,300, most preferably from about 3,000 to about 4,100. Ideally, such a polyol would contain predominantly secondary hydroxy groups.

If the process is utilized to produce a polyurea-modified polyurethane foam, the non-hydrophilic active hydrogen-containing compound comprises, at least in part, compounds wherein hydrogen is bonded to nitrogen. Preferably such compounds are selected from the group comprising polyamines, polyamides, polyimines and polyolamines, more preferably polyamines. Non-limiting examples of such compounds include primary and secondary amine terminated polyethers. Preferably such polyethers have a molecular weight of greater than about 1500, a functionality of from 2 to 6, and an amine equivalent weight of from about 200 to about 6,000. Such amine terminated polyethers are typically made from an appropriate initiator to which a lower alkylene (e.g. ethylene, propylene, butylene and mixtures thereof) oxide is added with the resulting hydroxyl terminated polyol being subsequently aminated. If two or more alkylene oxides are used, they may be present either as random mixtures or as blocks of one or the other polyether. For ease of amination, it is especially preferred that the hydroxyl groups of the polyol be essentially all secondary hydroxyl groups. Typically, the amination step replaces the majority but not all of the hydroxyl groups of the polyol.

The superabsorbent material used in the uniform mixture is capable of absorbing at least about 20 times its weight of an aqueous fluid maintained at a temperature in the range of from about 20° to about 25° C. Preferably, the superabsorbent material is a synthetic polymer such as a cellulosic polymer or a polymer of at least one of an acrylic monomer and vinyl monomer. A non-limiting example of a suitable cellulosic polymer is a carboxymethyl cellulose. A non-limiting example of a suitable polymer of at least one of an acrylic monomer and vinyl monomer may be selected from the group consisting of polyvinylpyrrolidone, sulfonated polystyrene, polysulfethyl acrylate, poly(2-hydroxyethylacrylate), polyacrylamide, polyacrylic acid, poly(acrylic acid alkali metal salt), starch modified polyacrylic acid, poly(starch modified acrylic acid alkali metal salt), hydrolyzed polyacrylonitrile, poly(hydrolyzed polyacrylonitrile alkali metal salt) and mixtures thereof. Most preferably, the superabsorbent material is a poly(acrylic acid alkali metal salt) such poly(sodium acrylate).

While the amount of superabsorbent material used in the initial step in the present process is not particularly restricted, it is preferred that the superabsorbent material be present in an amount up to about 100 parts by weight per hundred parts by weight of active hydrogen-containing compound used to produce the foamed isocyanate-based polymer. More preferably, the superabsorbent material is present in an amount in the range of from about 20 to about 80 parts, more preferably from about 35 to about 75, most preferably from about 55 to about 65, by weight per hundred parts by weight of active hydrogen-containing compound used to produce the foamed isocyanate-based polymer.

The manner by which the uniform mixture of isocyanate, active hydrogen-containing compound and superabsorbent material is prepared is not particularly restricted. Thus, it is possible to preblend the components in a separate tank which is then connected to a suitable mixing device for mixing with the aqueous blowing agent and catalyst. Alternatively, it is possible to preblend the superabsorbent material with the active hydrogen-containing compound. This preblend could then be fed to a suitable mixhead which would also receive independent streams of the isocyanate, the aqueous blowing agent and the catalyst (the aqueous blowing agent and catalyst streams could be combined prior to the mixhead, if desired). In this embodiment, care would have to taken to design the mixhead to ensure that the preblend and isocyanate streams are adequately mixed at the time that the aqueous blowing agent and catalyst stream(s) are added.

As is known in the art, aqueous blowing agents such as water can be used as a reactive blowing agent in the production of foamed isocyanate-based polymers. Specifically, water reacts with the isocyanate forming carbon dioxide which acts as the effective blowing agent in the final foamed polymer product. Optionally, organic blowing agents may be used in conjunction with the aqueous blowing agent, although the use of such blowing agents is generally being curtailed for environmental considerations. It is known in the art that the amount of water used as a blowing agent in the preparation of a foamed isocyanate-based polymer is conventionally in the range of from about 0.5 to as high as about 40 or more parts by weight, preferably from about 1.0 to about 10 parts by weight, based on 100 parts by weight of the total active hydrogen-containing compound content in the reaction mixture. Since the amount of water used in the production of a foamed isocyanate-based polymer is limited by the fixed properties expected in the foamed polymer, it may be necessary, in certain circumstances, to utilize a substantially inert liquid extenders when high loadings of filler material are contemplated. Non-limiting examples of suitable liquid extenders include halogenated hydrocarbons, high molecular weight hydrocarbons and polyols.

The catalyst added to the uniform mixture of isocyanate, active hydrogen-containing compound and superabsorbent material is a compound capable of catalyzing the polymerization reaction. Such catalysts are known, and the choice and concentration thereof is within the purview of a person skilled in the art. See for example U.S. Pat. Nos. 4,296,213 and 4,518,778, the contents of each of which is incorporated herein by reference. Non-limiting examples of suitable catalysts include tertiary amines and/or organometallic compounds. Additionally, as is known in the art, when the objective is to produce an isocyanurate, a Lewis acid must be used as the catalyst, either alone or in conjunction with other catalysts. Of course it will be understood by those skilled in the art that a combination of two or more catalysts may be suitably used.

As will be clearly understood by those of skill in the art, it is contemplated that conventional additives in the isocyanate-based polymer art be used in the process. Non-limiting examples of such additives include: surfactants (e.g. organo-silicone compounds available under the tradename L-540 Union Carbide), cell openers (e.g. silicone oils), extenders (e.g. halogenated paraffins commercially available as Cereclor S45), cross-linkers (e.g. low molecular weight reactive hydrogen-containing compositions), pigments/ dyes, flame retardants (e.g. halogenated organo-phosphoric acid compounds), inhibitors (e.g. weak acids), nucleating agents (e.g. diazo compounds), anti-oxidants, and plasticizers/stabilizers (e.g. sulphonated aromatic compounds). The amounts of these additives conventionally used would be within the purview of a person skilled in the art.

Once the aqueous blowing agent and catalyst have been added to the uniform mixture of isocyanate, active hydrogen-containing compound and superabsorbent material, a reaction mixture is formed. This reaction mixture is then expanded to produce the present foamed isocyanate-based polymer. As will be apparent to those of skill in the art, the process of the present invention is useful in the production of slab foam, moulded articles, carpet underlay and the like. Thus, as will be apparent to a person skill in the art, the manner by which expansion of the reaction mixture is effected will be dictated by the type of foam being produced.

The product of the present process is a foamed isocyanate-based polymer having a cellular structure and containing a superabsorbent material, the polymer being capable of: (i) absorbing at least about 20 times its weight of an aqueous fluid maintained at a temperature of from about 20° to about 25° C., and (ii) retaining at least about 20 times its weight of absorbed aqueous fluid which is bound to the superabsorbent material. Preferably the polymer is capable of: (i) absorbing at from about 20 to about 100, more preferably from about 20 to about 80, most preferably from about 35 to about 65, times its weight of an aqueous fluid maintained at a temperature of from about 20° to about 25° C., and (ii) retaining from about 20 to about 90, more preferably from about 20 to about 70, most preferably from about 30 to about 55, times its weight of absorbed aqueous fluid which is bound to the superabsorbent material.

The ability of the foamed isocyanate-based polymer to absorb aqueous liquid can be assessed by following protocol: (i) weigh test sample of foamed isocyanate-based polymer ($W_i$), (ii) immerse test sample in an aqueous fluid maintained at a temperature of from about 20° to about 25° C. for a period of at least 30 minutes, (iii) remove test sample from aqueous .fluid and maintained on drip screen or similar device for 3 minutes, (iv) weigh test sample ($W_f$), and (iv) calculate ($W_f$-$W_i$)/$W_i$ and report as the amount of aqueous fluid absorbed as a multiple of the weight of the original test sample of foamed isocyanate-based polymer ($W_i$) (another way in which to report the results is as units mass of aqueous liquid absorbed per unit mass of foam). The ability of the foamed isocyanate-based polymer to retain aqueous liquid can be assessed by conducting the absorption protocol and the following subsequent steps: (v) compress the absorbed test sample until no more aqueous fluid can be forcibly expelled from the test sample, (vi) weigh test sample ($W_r$), and (iv) calculate ($W_r$-$W_i$)/$W_i$ and report as the amount of aqueous fluid retained as a multiple of the weight of the original test sample of foamed isocyanate-based polymer ($W_i$) (another way in which to report the results is as units mass of aqueous liquid retained per unit mass of foam). Thus, the two protocols distinguish between aqueous fluid which is physically and chemically bound to the foam (i.e. absorbed) and aqueous fluid which only chemically bound to the foam (i.e. retained).

The type of superabsorbent material and the amount thereof present in the foamed isocyanate-based polymer is as discussed hereinabove in regard to the present process.

Embodiments of the present invention will now be described with reference to the following Examples which should not be construed as limiting the scope of the invention. The term "pbw" used in the Examples refers to parts by weight.

In the Examples the following compounds were used:

1. DABCO-T16, a polymerization catalyst commercially available from Air Products and Chemicals, Inc.;

2. Z65, a tertiary amine catalyst commercially available under the trade name JEFFCAT from Huntsman Corporation;

3. B8202, a surfactant commercially available from Goldschmidt Chemical Corporation;

4. CP1421, a hydrophilic polyether polyol having a molecular weight of approximately 5,000 and an ethylene oxide content of approximately 80% by weight, available from The Dow Chemical Company;

5. VORANOL 3010, a non-hydrophilic polyether polyol having a molecular weight of approximately 3000 and an ethylene oxide content of less than about 20% by weight, commercially available from The Dow Chemical Company;

6. HS100, a non-hydrophilic polyether polyol which is a blend of 3010 and polymeric solids, commercially available from Arco Chemical Company;

7. TDI 80, a blend of 80% by weight 2,4-toluene diisocyanate, and 20% by weight 2,6-toluene diisocyanate commercially available from Miles Inc. under the tradename Mondur TD-80 Grade A; and 8. SXM-75, a poly(sodium acrylate) compound available from Stockhausen Inc.

EXAMPLES 1–10

In these Examples, a series of hydrophilic polyurethane foams containing various amounts of superabsorbent materials were prepared. The general formulation used is provided in Table 1. The amount of superabsorbent material used in each Example is provided in Table 2.

TABLE 1

| Ingredient | Amount (pbw) |
|---|---|
| CP1421 | 75.0 |
| VORANOL 3010 | 25.0 |
| B8202 | 1.3 |
| Z65 | 0.5 |
| DABCO-T16 | 0.05 |
| $H_2O$ | 3.60 |
| TDI 80 | Amount sufficient to achieve an isocyanate index of about 1.05 |

The foams were prepared by blending the two polyols with the superabsorbent material to which was added the isocyanate to form a uniform mixture. The remaining ingredients, including the catalyst and water blowing agent, were blended separately and then added to the uniform mixture of polyols, superabsorbent material and isocyanate with adequate mixing to provide a uniform reaction mixture. The reaction mixture was poured into an open container and allowed to expand to result in a polyurethane foam.

Each foam was cut to provide triplicate samples having the following dimensions: 3"×5"×½". The water absorption and retention properties of each of the triplicate samples was assessed using the absorption and retention protocols described above. The aqueous liquid was water and the immersion time was 60 minutes. The results, reported for each Example as the average absorption and retention, respectively, for the triplicate samples, are provided in Table 2.

TABLE 2

| Example | SXM-75 (pbw) | Absorption | Retention |
| --- | --- | --- | --- |
| 1 | 0 | 8.9 | 2.0 |
| 2 | 19.0 | 35.1 | 28.8 |
| 3 | 29.0 | 42.3 | 34.3 |
| 4 | 48.0 | 46.3 | 37.9 |
| 5 | 50.0 | 49.5 | 39.2 |
| 6 | 60.0 | 57.7 | 47.4 |
| 7 | 65.0 | 54.2 | 43.6 |
| 8 | 71.5 | 54.2 | 46.3 |
| 9 | 85.0 | 54.2 | 44.2 |
| 10 | 100.0 | 54.9 | 45.2 |

As will be apparent to those of skill in the art, Example 1 contains no superabsorbent material and is provided for comparison purposes only. The results clearly demonstrate that the foams produced in Examples 2–10 exhibit significantly improved absorption and retention properties compared to a hydrophilic foam which does not contain a superabsorbent material (Example 1).

EXAMPLES 11–14

In these Examples, the methodology of Examples 1–10 was repeated except a mixture of non-hydrophilic polyols was used in place of the hydrophilic polyol/non-hydrophilic polyol mixture used in Examples 1–10. Accordingly, it will be understood by those of skill in the art that Examples 11–14 are for comparative purposes only. The general formulation used in Examples 11–14 is provided in Table 3. The amount of superabsorbent material used in each Example is provided in Table 4.

The foams produced in these Examples 11–14 were tested for water absorption and retention properties using the protocol described in Examples 1–10. The results are provided in Table 4 and demonstrate the importance of using a hydrophilic polyol in the formulation. Specifically, the absorption and retention properties of the foams produced in Examples 2–10 are almost twice those of the foams produced in Examples 11–14. Further, a comparison of the absorption and retention properties of (i) the foam produced in Example 1 and any of the foams produced in Examples 11–14, with (ii) the foams produced in Examples 2–10 (i.e. exemplary foams in accordance with the present invention), demonstrates that the improvements in water absorption and retention are synergistic.

TABLE 3

| Ingredient | Amount (pbw) |
| --- | --- |
| HS100 | 60.0 |
| VORANOL 3010 | 40.0 |
| B8202 | 1.0 |
| Z65 | 0.45 |
| DABCO-T16 | 0.48 |
| H$_2$O | 3.60 |
| TDI 80 | Amount sufficent to achieve an isocyanate index of about 1.12 |

TABLE 4

| Example | SXM-75 (pbw) | Absorption | Retention |
| --- | --- | --- | --- |
| 11 | 0 | 11.7 | 1.4 |
| 12 | 29.0 | 18.9 | 13.2 |
| 13 | 48.0 | 19.5 | 14.4 |
| 14 | 60.0 | 19.1 | 14.4 |

What is claimed is:

1. A foamed isocyanate-based polymer having a cellular structure and containing a superabsorbent material, the polymer being capable of: (i) absorbing at least about 20 times its weight of water maintained at a temperature of from about 20° to about 25° C., and (ii) retaining at least about 20 times its weight of absorbed water which is bound to the superabsorbent material, the foamed isocyanate-based polymer being based on an active hydrogen-containing compound comprising from about 20% to about 90% by weight of a hydrophilic active hydrogen-containing compound and from about 10% to about 80% by weight of a non-hydrophilic active hydrogen-containing compound.

2. The foamed isocyanate-based polymer defined in claim 1, wherein the polymer is capable of: (i) absorbing from about 20 to about 100 times its weight of water maintained at a temperature of from about 20° to about 25° C., and (ii) retaining from about 20 to about 90 times its weight of absorbed water which is bound to the superabsorbent material.

3. The foamed isocyanate-based polymer defined in claim 1, wherein the polymer is capable of: (i) absorbing from about 20 to about 80 times its weight of water maintained at a temperature of from about 20° to about 25° C., and (ii) retaining from about 20 to about 70 times its weight of absorbed water which is bound to the superabsorbent material.

4. The foamed isocyanate-based polymer defined in claim 1, wherein the polymer is capable of: (i) absorbing from about 35 to about 65 times its weight of water maintained at a temperature of from about 20° to about 25° C., and (ii) retaining from about 30 to about 55 times its weight of absorbed water which is bound to the superabsorbent material.

5. The foamed isocyanate-based polymer defined in claim 1, wherein the superabsorbent material is a synthetic polymer.

6. The foamed isocyanate-based polymer defined in claim 1, wherein the superabsorbent material is a cellulosic polymer.

7. The foamed isocyanate-based polymer defined in claim 1, wherein the cellulosic polymer is a carboxymethyl cellulose.

8. The foamed isocyanate-based polymer defined in claim 1, wherein the superabsorbent material is selected from a polymer of an acrylic monomer or a polymer of a vinyl monomer.

9. The foamed isocyanate-based polymer defined in claim 1, wherein the superabsorbent material is selected from the group consisting of polyvinylpyrroli-done, sulfonated polystyrene, polysulfethyl acrylate, poly(2-hydroxyethylacrylate), polyacrylamide, polyacrylic acid, poly(acrylic acid alkali metal salt), starch modified polyacrylic acid, poly(starch modified acrylic acid alkali metal salt), hydrolyzed polyacrylonitrile, poly(hydrolyzed polyacrylonitrile alkali metal salt) and mixtures thereof.

10. The foamed isocyanate-based polymer defined in claim 1, wherein the superabsorbent material is present in an amount up to about 100 parts by weight per hundred parts by weight of active hydrogen-containing compound used to produce the foamed isocyanate-based polymer.

11. The foamed isocyanate-based polymer defined in claim 1, wherein the superabsorbent material is present in the range of from about 20 to about 80 parts by weight per hundred parts by weight of active hydrogen-containing compound used to produce the foamed isocyanate-based polymer.

12. The foamed isocyanate-based polymer defined in claim 1, wherein the superabsorbent material is present in the range of from about 35 to about 75 parts by weight per hundred parts by weight of active hydrogen-containing compound used to produce the foamed isocyanate-based polymer.

13. The foamed isocyanate-based polymer defined in claim 1, wherein the superabsorbent material is present in the range of from about 55 to about 65 parts by weight per hundred parts by weight of active hydrogen-containing compound used to produce the foamed isocyanate-based polymer.

14. The foamed isocyanate-based polymer defined in claim 1, wherein the active hydrogen-containing compound comprises from about 40% to about 90% by weight of a hydrophilic active hydrogen-containing compound and from about 10% to about 60% by weight of a non-hydrophilic active hydrogen-containing compound.

15. The foamed isocyanate-based polymer defined in claim 1, wherein the active hydrogen-containing compound comprises from about 70% to about 80% by weight of a hydrophilic active hydrogen-containing compound and from about 20% to about 30% by weight of a non-hydrophilic active hydrogen-containing compound.

16. The foamed isocyanate-based polymer defined in claim 1, wherein the hydrophilic active hydrogen-containing compound is a hydrophilic polyol.

17. The foamed isocyanate-based polymer defined in claim 16, wherein the hydrophilic polyol is selected from the group consisting of diols, triols and tetrols, the hydrophilic polyol containing polyoxyalkylene groups, the polyoxyalkylene groups comprising at least 25 percent by weight of ethylene oxide.

18. The foamed isocyanate-based polymer defined in claim 16, wherein the hydrophilic polyol is selected from the group consisting of diols, triols and tetrols, the hydrophilic polyol containing polyoxyalkylene groups, the polyoxyalkylene groups comprising from about 40 to about 85 percent by weight of ethylene oxide.

19. The foamed isocyanate-based polymer defined in claim 16, wherein the hydrophilic polyol is selected from the group consisting of diols, triols and tetrols, the hydrophilic polyol containing polyoxyalkylene groups, the polyoxyalkylene groups comprising from about 55 to about 85 percent by weight of ethylene oxide.

20. A polyurethane foam comprising poly(acrylic acid alkali metal salt) in an amount in the range of from about 55 to about 65 parts by weight per hundred parts by weight of polyol used to produce the foam, the foam being capable of: (i) absorbing from about 35 to about 65 times its weight of water maintained at a temperature of from about 20° to about 25° C., and (ii) retaining from about 30 to about 55 times its weight of absorbed water which is bound to the poly(acrylic acid alkali metal salt), the foam being expanded from a reaction mixture comprising an isocyanate and an active hydrogen-containing compound comprising from about 20% to about 90% by weight of a hydrophilic polyol and from 10% to about 80% by weight of a non-hydrophilic polyol, wherein the hydrophilic polyol is selected from the group consisting of diols, triols and tetrols, the hydrophilic polyol containing polyoxyalkylene groups, the polyoxyalkylene groups comprising at least 25 percent by weight of ethylene oxide.

21. A process for producing a foamed isocyanate-based polymer comprising the steps of:

providing a uniform mixture comprising an isocyanate, an active hydrogen-containing compound and a superabsorbent material, the superabsorbent material being capable of absorbing at least about 20 times its weight of an aqueous fluid maintained at a temperature in the range of from about 20° to about 25° C.;

adding to the uniform mixture an aqueous blowing agent and a catalyst to form a reaction mixture; and expanding the reaction mixture to produce the foamed isocyanate-based polymer;

wherein the active hydrogen-containing compound comprises from about 20% to about 90% by weight of a hydrophilic active hydrogen-containing compound and from about 10% to about 80% by weight of a non-hydrophilic active hydrogen-containing compound.

22. The process defined in claim 21, wherein the active hydrogen-containing compound comprises from about 40% to about 90% by weight of a hydrophilic active hydrogen-containing compound and from about 10% to about 60% by weight a of non-hydrophilic active hydrogen-containing compound.

23. The process defined in claim 21, wherein the active hydrogen-containing compound comprises from about 70% to about 80% by weight of a hydrophilic active hydrogen-containing compound and from about 20% to about 30% by weight a of non-hydrophilic active hydrogen-containing compound.

24. The process defined in claim 21, wherein the hydrophilic active hydrogen-containing compound is a hydrophilic polyol.

25. The process defined in claim 24, wherein the hydrophilic polyol is selected from the group consisting of diols, triols and tetrols, the hydrophilic polyol containing polyoxyalkylene groups, the polyoxyalkylene groups comprising at least 25 percent by weight of ethylene oxide.

26. The process defined in claim 21, wherein the non-hydrophilic active hydrogen-containing compound is selected from the group consisting of non-hydrophilic polyols, polyamines, polyamides, polyimines, polyolamines and mixtures thereof.

27. The process defined in claim 21, wherein the non-hydrophilic active hydrogen-containing compound is a non-hydrophilic polyol selected from the group consisting of polyether, polyesters, polycarbonate, polydiene, polycaprolactone and mixtures thereof.

28. The process defined in claim 27, wherein the non-hydrophilic polyol is selected from the group consisting of adipic acid-ethylene glycol polyester, poly(butylene glycol), poly(propylene glycol), hydroxyl-terminated polybutadiene and mixtures thereof.

29. The process defined in claim 29, wherein the non-hydrophilic polyol is a polyether polyol.

30. The process defined in claim 21, wherein the isocyanate is represented by the general formula:

wherein i is an integer of two or more and Q is an organic radical having the valence of i.

31. The process defined in claim 21, wherein the isocyanate is selected from the group consisting of 1,6-hexamethylene diisocyanate, 1,4-butylene diisocyanate, furfurylidene diisocyanate, 2,4-toluene diisocyanate, 2,6-toluene diisocyanate, 2,4'-diphenylmethane diisocyanate, 4,4'-diphenylmethane diisocyanate, 4,4'-diphenylpropane diisocyanate, 4,4'-diphenyl-3,3'-dimethyl methane diisocyanate, 1,5-naphthalene diisocyanate, 1-methyl-2,4-diisocyanate-5-chlorobenzene, 2,4-diisocyanato-s-triazine, 1-methyl-2,4-diisocyanato cyclohexane, p-phenylene diisocyanate, m-phenylene diisooyanate, 1,4-naphthalene diisocyanate, dianisidine diisocyanate, bitoluene diisocyanate, 1,4-xylylene diisocyanate, 1,3-xylylene diisocyanate, bis-(4-isocyanatophenyl)methane, bis-(3-methyl-4-isocyanatophenyl)methane, polymethylene polyphenyl polyisocyanates and mixtures thereof.

32. The process defined in claim 21, wherein the isocyanate is selected from the group consisting of 2,4-toluene diisocyanate, 2,6-toluene diisocyanate and mixtures thereof.

33. The process defined in claim 21, wherein the isocyanate is selected from the group consisting of (i) 2,4'-diphenylmethane diisocyanate, 4,4'-diphenylmethane diisocyanate and mixtures thereof; and (ii) mixtures of (i) with an isocyanate selected from the group comprising 2,4-toluene diisocyanate, 2,6-toluene diisocyanate and mixtures thereof.

34. A foamed isocyanate-based polymer having a cellular structure and containing a superabsorbent material, the polymer being capable of: (i) absorbing at least about 20 times its weight of water maintained at a temperature of from about 20° to about 25° C., and (ii) retaining at least about 20 times its weight of absorbed water which is bound to the superabsorbent material, the foamed isocyanate-based polymer being expanded from a reaction mixture comprising an isocyanate and an active hydrogen-containing compound comprising from about 20% to about 90% by weight of a hydrophilic active hydrogen-containing compound and from about 10% to about 80% by weight of a non-hydrophilic active hydrogen-containing compound.

35. The foamed isocyanate-based polymer defined in claim 34, wherein the polymer is capable of: (i) absorbing from about 20 to about 100 times its weight of water maintained at a temperature of from about 20° to about 25° C., and (ii) retaining from about 20 to about 90 times its weight of absorbed water which is bound to the superabsorbent material.

36. The foamed isocyanate-based polymer defined in claim 34 wherein the polymer is capable of: (i) absorbing from about 20 to about 80 times its weight of water maintained at a temperature of from about 20° to about 25° C., and (ii) retaining from about 20 to about 70 times its weight of absorbed water which is bound to the superabsorbent material.

37. The foamed isocyanate-based polymer defined in claim 34 wherein the polymer is capable of: (i) absorbing from about 35 to about 65 times its weight of water maintained at a temperature of from about 20° to about 25° C., and (ii) retaining from about 30 to about 55 times its weight of absorbed water which is bound to the superabsorbent material.

38. The foamed isocyanate-based polymer defined in claim 34, wherein the superabsorbent material is a synthetic polymer.

39. The foamed isocyanate-based polymer defined in claim 34, wherein the superabsorbent material is a cellulosic polymer.

40. The foamed isocyanate-based polymer defined in claim 39, wherein the cellulosic polymer is a carboxymethyl cellulose.

41. The foamed isocyanate-based polymer defined in claim 34, wherein the superabsorbent material is selected from a polymer of an acrylic monomer or a polymer of a vinyl monomer.

42. The foamed isocyanate-based polymer defined in claim 34, wherein the superabsorbent material is selected from the group consisting of polyvinylpyrrolidone, sulfonated polystyrene, polysulfethyl acrylate, poly(2-hydroxyethylacrylate), polyacrylamide, polyacrylic acid, poly(acrylic acid alkali metal salt), starch modified polyacrylic acid, poly(starch modified acrylic acid alkali metal salt), hydrolyzed polyacrylonitrile, poly(hydrolyzed polyacrylonitrile alkali metal salt) and mixtures thereof.

43. The foamed isocyanate-based polymer defined in claim 34, wherein the superabsorbent material is present in an amount up to about 100 parts by weight per hundred parts by weight of active hydrogen-containing compound used to produce the foamed isocyanate-based polymer.

44. The foamed isocyanate-based polymer defined in claim 34, wherein the superabsorbent material is present in the range of from about 20 to about 80 parts by weight per hundred parts by weight of active hydrogen-containing compound used to produce the foamed isocyanate-based polymer.

45. The foamed isocyanate-based polymer defined in claim 34, wherein the superabsorbent material is present in the range of from about 35 to about 75 parts by weight per hundred parts by weight of active hydrogen-containing compound used to produce the foamed isocyanate-based polymer.

46. The foamed isocyanate-based polymer defined in claim 34, wherein the superabsorbent material is present in the range of from about 55 to about 65 parts by weight per hundred parts by weight of active hydrogen-containing compound used to produce the foamed isocyanate-based polymer.

47. The foamed isocyanate-based polymer defined in claim 34, wherein the active hydrogen-containing compound comprises from about 4.0% to about 90% by weight of a hydrophilic active hydrogen-containing compound and from about 10% to about 60% by weight of a non-hydrophilic active hydrogen-containing compound.

48. The foamed isocyanate-based polymer defined in claim 34, wherein the active hydrogen-containing compound comprises from about 70% to about 80% by weight of a hydrophilic active hydrogen-containing compound and from about 20% to about 30% by weight of a non-hydrophilic active hydrogen-containing compound.

49. The foamed isocyanate-based polymer defined in claim 34, wherein the hydrophilic active hydrogen-containing compound is a hydrophilic polyol.

50. The foamed isocyanate-based polymer defined in claim 49, wherein the hydrophilic polyol is selected from the group consisting of diols, triols and tetrols, the hydrophilic polyol containing polyoxyalkylene groups, the polyoxyalkylene groups comprising at least 25 percent by weight of ethylene oxide.

51. The foamed isocyanate-based polymer defined in claim 49, wherein the hydrophilic polyol is selected from the group consisting of diols, triols and tetrols, the hydrophilic polyol containing polyoxyalkylene groups, the polyoxyalkylene groups comprising from about 40 to about 85 percent by weight of ethylene oxide.

52. A polyurethane foam having a cellular structure and containing a superabsorbent material, the foam being capable of: (i) absorbing at least about 20 times its weight of water maintained at a temperature of from about 20° to about 25° C., and (ii) retaining at least about 20 times its weight of absorbed water which is bound to the superabsorbent material, the foam being expanded from a reaction mixture comprising an isocyanate and an active hydrogen-containing compound comprising from about 20% to about 90% by weight of a hydrophilic polyol and from about 10% to about 80% by weight of a non-hydrophilic polyol, wherein the hydrophilic polyol is selected from the group consisting of diols, triols and tetrols, the hydrophilic polyol containing polyoxyalkylene groups, the polyoxyalkylene groups comprising at least 25 percent by weight of ethylene oxide.

53. The polyurethane foam defined in claim 52, wherein the foam is capable of: (i) absorbing from about 20 to about 100 times its weight of water maintained at a temperature of from about 20° to about 25° C., and (ii) retaining from about 20 to about 90 times its weight of absorbed water which is bound to the superabsorbent material.

54. The polyurethane foam defined in claim 52, wherein the foam is capable of: (i) absorbing from about 20 to about 80 times its weight of water maintained at a temperature of from about 20° to about 25° C., and (ii) retaining from about 20 to about 70 times its weight of absorbed water which is bound to the superabsorbent material.

55. The polyurethane foam defined in claim 52, wherein the polymer is capable of: (i) absorbing from about 35 to about 65 times its weight of water maintained at a temperature of from about 20° to about 25° C., and (ii) retaining from about 30 to about 55 times its weight of absorbed water which is bound to the superabsorbent material.

56. The polyurethane foam defined in claim 52, wherein the superabsorbent material is a synthetic polymer.

57. The polyurethane foam defined in claim 52, wherein the superabsorbent material is a cellulosic polymer.

58. The polyurethane foam defined in claim 57, wherein the cellulosic polymer is a carboxymethyl cellulose.

59. The foamed isocyanate-based polymer defined in claim 52, wherein the superabsorbent material is selected from a polymer of an acrylic monomer or a polymer of a vinyl monomer.

60. The polyurethane foam defined in claim 52, wherein the superabsorbent material is selected from the group consisting of polyvinylpyrrolidone, sulfonated polystyrene, polysulfethyl acrylate, poly(2-hydroxyethylacrylate), polyacrylamide, polyacrylic acid, poly(acrylic acid alkali metal salt), starch modified polyacrylic acid, poly(starch modified acrylic acid alkali metal salt), hydrolyzed polyacrylonitrile, poly(hydrolyzed polyacrylonitrile alkali metal salt) and mixtures thereof.

61. The polyurethane foam defined in claim 52, wherein the superabsorbent material is present in an amount up to about 100 parts by weight per hundred parts by weight of active hydrogen-containing compound used to produce the polyurethane foam.

62. The polyurethane foam defined in claim 52, wherein the superabsorbent material is present in the range of from about 20 to about 80 parts by weight per hundred parts by weight of active hydrogen-containing compound used to produce the polyurethane foam.

63. The polyurethane foam defined in claim 52, wherein the superabsorbent material is present in the range of from about 35 to about 75 parts by weight per hundred parts by weight of active hydrogen-containing compound used to produce the polyurethane foam.

64. The polyurethane foam defined in claim 52, wherein the superabsorbent material is present in the range of from about 55 to about 65 parts by weight per hundred parts by weight of active hydrogen-containing compound used to produce the polyurethane foam.

65. The polyurethane foam defined in claim 52, wherein the active hydrogen-containing compound comprises from about 40% to about 90% by weight of the hydrophilic polyol and from about 10% to about 60% by weight of the non-hydrophilic polyol.

66. The polyurethane foam defined in claim 52, wherein the active hydrogen-containing compound comprises from about 70% to about 80% by weight of the hydrophilic polyol and from about 20% to about 30% by weight of the non-hydrophilic polyol.

67. The polyurethane foam defined in claim 62, wherein ,the polyoxyalkylene groups in the hydrophilic polyol comprise from about 40 to about 85 percent by weight of ethylene oxide.

68. A personal hygiene device having a bodily fluid absorbent layer consisting essentially of the foamed isocyanate-based polymer defined in claim 1.

69. A personal hygiene device having a bodily fluid absorbent layer consisting essentially of the foamed polyurethane polymer defined in claim 20.

* * * * *